United States Patent [19]

Malis et al.

[11] Patent Number: 5,012,811

[45] Date of Patent: May 7, 1991

[54] FETAL ELECTRODE PRODUCT WITH PROTECTIVE CAP

[75] Inventors: Michael J. Malis, Trumbull; Flave L. Jones, Guilford, both of Conn.

[73] Assignee: American Home Products Corporation, New York, N.Y.

[21] Appl. No.: 287,269

[22] Filed: Dec. 20, 1988

Related U.S. Application Data

[63] Continuation-in-part of Ser. No. 154,639, Feb. 9, 1988, abandoned.

[51] Int. Cl.$^5$ .............................. A61B 5/04
[52] U.S. Cl. ................................. 128/642
[58] Field of Search ............. 128/639, 640, 642, 785, 128/786, 419 P

[56] References Cited

U.S. PATENT DOCUMENTS

| | | | |
|---|---|---|---|
| Re. 28,990 | 10/1976 | Hon et al. | 128/642 |
| 2,208,023 | 7/1940 | Ellis | 128/639 |
| 4,046,151 | 9/1977 | Rose | 128/404 |
| 4,180,080 | 12/1979 | Murphy | 128/642 |
| 4,281,659 | 8/1981 | Farrar et al. | 128/635 |
| 4,321,931 | 3/1982 | Hon | 128/642 |
| 4,649,938 | 3/1987 | McArthur | 128/785 |
| 4,743,233 | 5/1988 | Schneider | 604/192 |
| 4,819,661 | 4/1989 | Heil, Jr. et al. | 128/639 |
| 4,836,208 | 6/1989 | Ulbrich | 128/642 |

FOREIGN PATENT DOCUMENTS 2738479 3/1979 Fed. Rep. of Germany ...... 128/642

Primary Examiner—Lee S. Cohen
Assistant Examiner—Kevin Pontius
Attorney, Agent, or Firm—Darby & Darby

[57] ABSTRACT

A fetal electrode product comprises a guide tube, an electrode assembly having a spiral electrode extending from its forward end and a flexible drive tube extending through said guide tube and adapted to engage said electrode assembly for rotating said spiral electrode. A protective cap is retained on the forward portion of the electrode assembly to protect the doctor and mother from the pointed end of the spiral electrode before, during and after the electrode is removed from the fetus during birth.

4 Claims, 2 Drawing Sheets

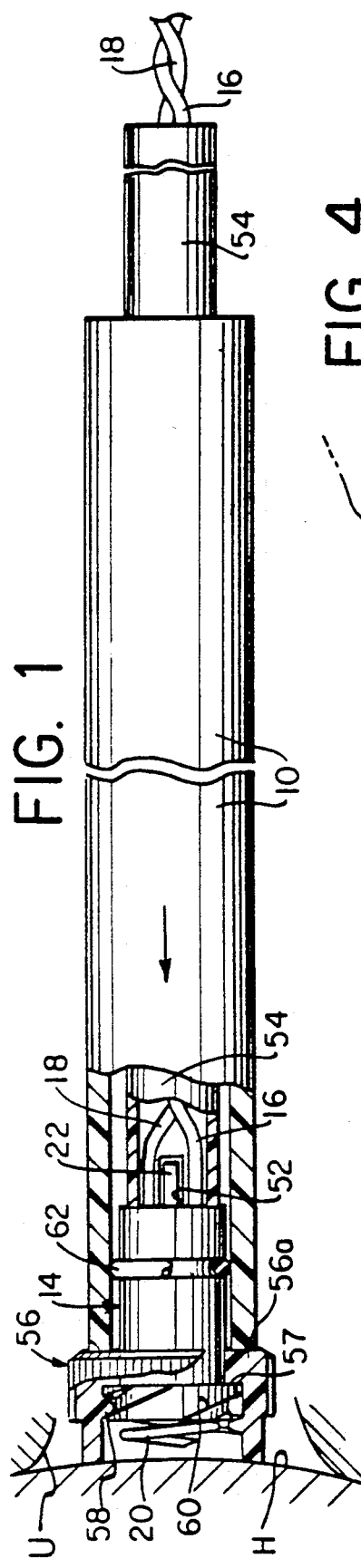
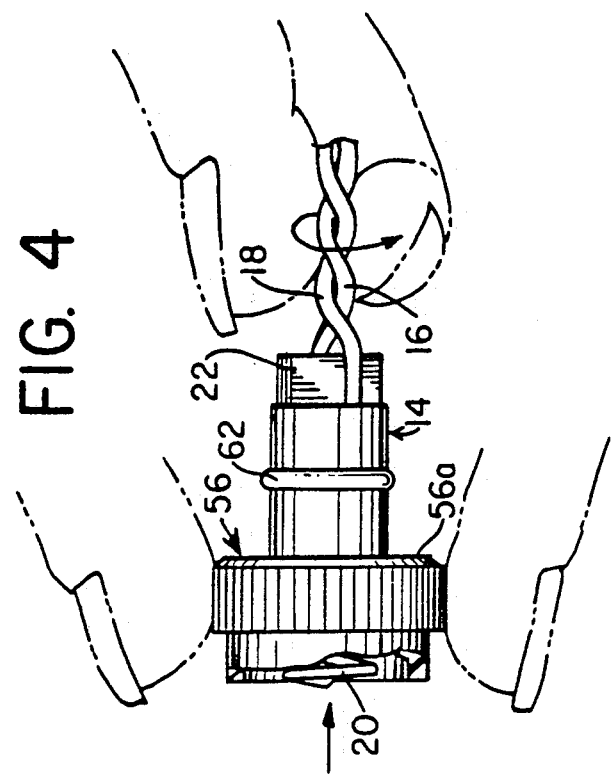
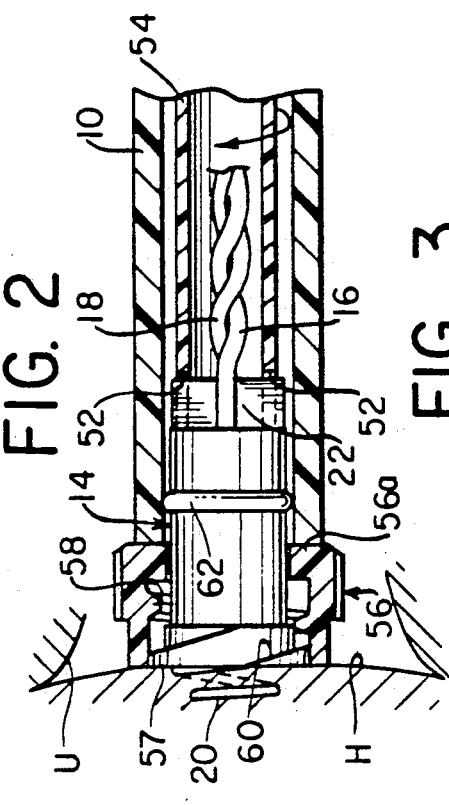
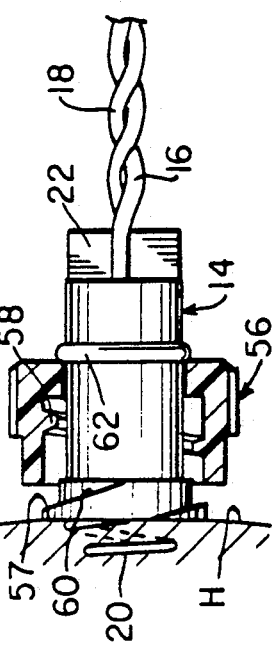

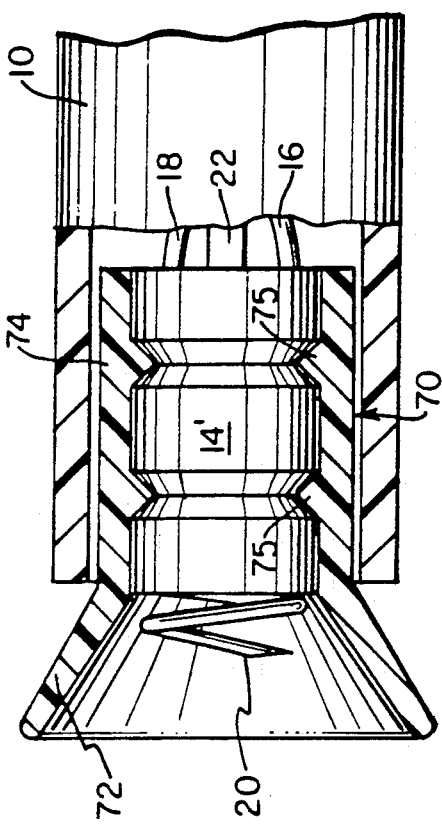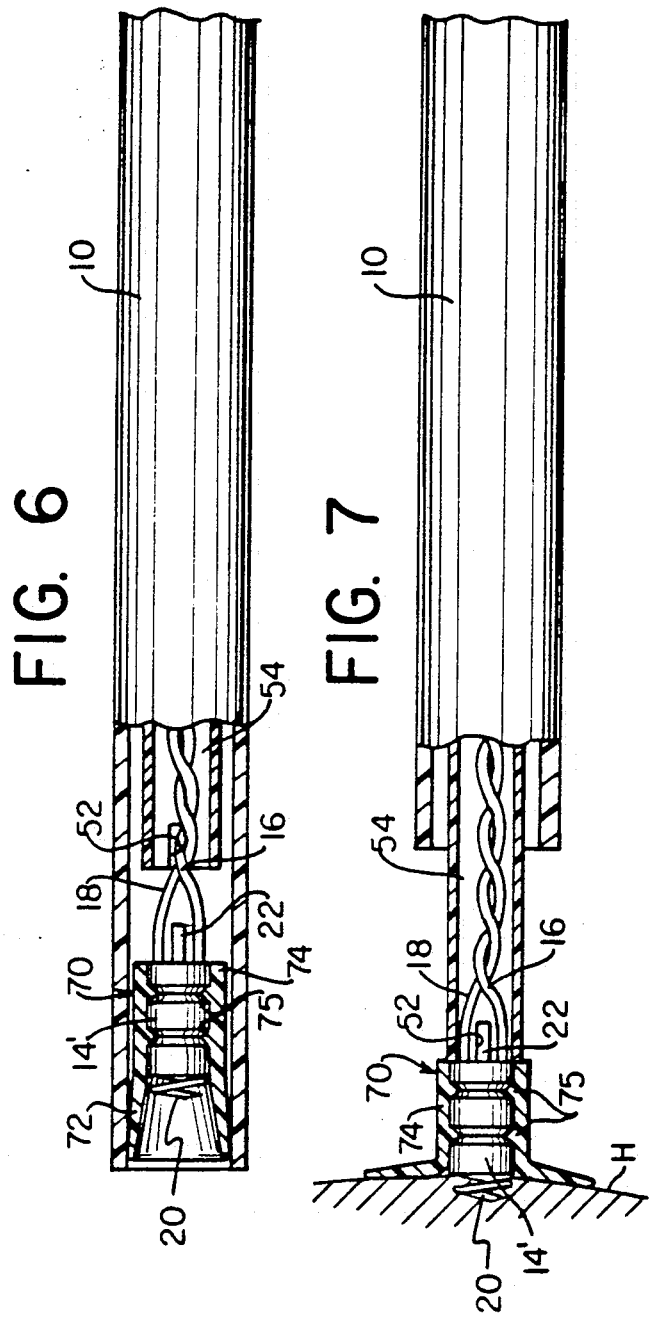

FETAL ELECTRODE PRODUCT WITH PROTECTIVE CAP

This application is a continuation in part of application Ser. No. 154,639 filed on Feb. 9, 1988, now abandoned.

This invention pertains to fetal electrodes. More particularly, this invention relates to a safety feature for use with fetal electrodes of the type shown in U.S. Reissue Pat. No. 28,990 of Hon et al reissued on Oct. 5, 1976.

BACKGROUND

FIGS. 8-10 of U.S. Reissue Pat. No. 28,990 illustrate the fetal electrode most commonly used in the United States today. The product comprises a curved form sustaining guide tube through which an electrode assembly can be delivered to a fetal presenting part (typically the scalp) during delivery. The electrode which engages the fetus is a coil that extends from the forward end of an electrode holder and can be rotated by means of a flexible drive tube passing through the guide tube and adapted to engage a plate-like maternal electrode extending from the rear of the plastic holder.

The electrode is attached to the fetus by turning the drive tube causing the spiral electrode to penetrate the fetal presenting part. After the electrode is attached, the guide tube and drive tube are removed leaving the electrode in place. Wires attached to the coil and maternal electrode are then attached to a fetal monitor so that the condition of the fetus can be monitored prior to birth.

During birth, the coil is removed from the fetus by unscrewing it. When this is done, because the sharp point of the coil is unprotected, it can cause injury to the physician or the patient.

The object of this invention is to provide a safety device which can be used to sheath the coil of a spiral electrode to prevent injury to the patient and physician both before and after the electrode is attached or removed from the fetus.

SUMMARY OF THE INVENTION

According to the invention, a protective cap is mounted on the electrode assembly of a spiral electrode. In one embodiment, the cap is axially movable with respect to the spiral electrode so that it sheaths the electrode both during application of the electrode and removal. In another embodiment, a protective cover made of a flexible material is fixed to the electrode holder so that it sheaths the electrode prior to application as well as during application and removal.

BRIEF DESCRIPTION OF THE DRAWINGS

FIG. 1 is a side elevational view, partially in section, showing a first embodiment of the invention;

FIG. 2 is a corresponding view of the first preferred embodiment of the invention after the coil has been attached to the fetal presenting part;

FIG. 3 shows the electrode in place after the drive tube and guide tube have been removed;

FIG. 4 shows how the operator positions the protective cap of the first embodiment in accordance with the invention to sheath the coil when the electrode is to be removed;

FIG. 5 is a sectional view of a second and preferred embodiment of the invention showing a protective cover affixed to the electrode holder;

FIG. 6 is a sectional view of the second embodiment showing the protective cover within the guide tube; and FIG. 7 is a sectional view of the second embodiment showing the protective cover compressed outward upon the fetal epidermis and the electrode attached to the fetus.

DETAILED DESCRIPTION

A guide tube constructed in accordance with the invention can be used with electrodes other than the spiral electrode shown in the '990 patent; however, since that is the preferred version of the electrode it is illustrated in the drawings.

Referring to FIGS. 1-4, the electrode product includes a guide tube 10 having an open forward end through which a holder member 14 is adapted to pass. The holder member 14 has a spiral electrode 20 mounted in its forward end and a flat maternal electrode 22 mounted in its rear end.

The diameter of the cylindrical holder member 14 approximates the inner diameter of guide tube 10. Consequently, the holder member prevents lateral movement of the electrode coil 20 (relative to the guide tube) while the coil is being attached to the fetus. Moreover, the length of the holder member 14 is such that when the spiral electrode 20 extends just beyond the end of the guide tube 10 (for attachment to the fetus), the cylindrical holder member within the guide tube prevents skewing of the coil. These features help to reduce the possibility of injury to the fetus when the electrode is being applied.

A first electrode wire 16 extends through the rear end of the holder member 14 and is electrically connected to the rear end of spiral electrode 20. A second electrode wire 18 also extends through the rear end of holder member 14 and is electrically connected to the forward end of the second electrode 22.

Both electrodes 20 and 22 are preferably constructed of stainless steel and are soldered to their respective electrode wires 16 and 18. The holder member 14 is made of an insulating material, such as plastic, and electrically isolates the electrodes 20 and 22 from one another.

A flexible drive tube 54 is slidably and rotatably disposed in the guide tube 10 for rotating the holder 14 to screw the spiral electrode 20 into a fetal epidermis. The forward end of the drive tube 54 is provided with a pair of slots 52 which are adapted to receive the rearwardly extending portion of the plate electrode 22. When the slots 52 on the forward end of the drive tube 54 engage the plate electrode 22, the holder 14 and spiral electrode 20 may be rotated by rotating the flexible drive tube 54.

A cylindrical grip (not shown) may be attached to the rear of drive tube 54. The electrode wires 16 and 18 extend rearwardly through a releasable wire clamp (not shown) at the back of the drive tube 54 which extends from the rear portion of the guide tube 10 for connection to a suitable apparatus (not shown) for monitoring fetal heartbeat.

According to the first embodiment of the invention, a protective cap 56 is mounted on the holder member 14. In this preferred embodiment which is shown in FIGS. 1-4, the protective cap 56 may be cylindrical in shape and long enough to extend just beyond the sharp point of coil 20. The holder member 14 includes an enlarged forward head portion 57 which contains a helical groove 60. The groove 60 mates with a complementary helical rib 58 on the interior surface of the cap 56 to retain the cap in its protective position and cause axial movement of the two parts when one is rotated relative to the other. As best shown in FIGS. 2 and 3, the closed end 56a of the cap 56 fits snugly on the holder member 14. When rib 58 and groove 60 are disengaged, longitudinal movement of holder member 14 relative to the cap 56 away from the fetus (i.e., movement of cap 56 to the left) is limited by abutment of the head 57 against the top 56a of the cap. A retaining ring 62 extends circumferentially around the holder member 14 toward the rear thereof. The ring 62 protrudes slightly to function as a stop or retainer abutting against the top 56a of cap 56 to limit its rearward movement (i.e., movement of cap 56 to the right) on the holder member when rib 58 and groove 60 are disengaged.

FIGS. 1-4 also illustrate the first embodiment in actual use, with the fetal presenting part (typically the head) indicated by the letter H and the mother's uterus by the letter U. The physician receives the fetal electrode product with the cap 56 in the position shown in FIG. 1, i.e., with rib 58 threadedly engaging groove 60 so that cap 56 sheathes coil 20. With the spiral electrode 20, holder 14 and plate electrode 22 disposed as shown in FIG. 1, the doctor inserts the cap 56 and guide tube 10 through the woman's vagina and cervix until the forward end of the cap 56 makes contact with the fetal head (or other portion of the fetus). Using cap 56 as a stabilizing platform, the physician then applies the electrode by rotating the drive tube 54. As shown in FIG. 2, the rotation of the holder member 14 causes the coil 20 to engage and penetrate the fetus H. As the holder member 14 rotates with cap 56 stationary, the threaded engagement of rib 58 and groove 60 causes axial displacement of cap 56 relative to holder member 14 until the rib 58 and groove 60 are disengaged, at which point cap 56 can then slide on holder member 14. After the electrode is in place, guide tube 10 and drive tube 54 are removed in conventional fashion. The protective cap 56 will stay in place because of the ring 62 (see FIG. 3). During birth, when it is desired to remove the electrode from the fetus, the physician grasps the cap 56 with one hand (FIG. 4) and twists the wires 16 and 18 with the other hand to unscrew the coil from the fetus. As the coil is rotated, groove 60 is threaded back onto the helical rib 58 of protective cap 56 until the coil is once again sheathed by cap 56. Hence, the electrode coil is not likely to contact either the physician or the mother and the electrode can be removed without fear of injury.

In the preferred embodiment of the invention, shown in FIGS. 5-8, the protective cap is in the form of a flared cylinder 70 made of a flexible material such as silicone. The cylinder 70 comprises a flared, conically shaped portion 72 and a tubular portion 74 having internal ridges 75 adapted to be retained in complementary grooves (not numbered) within the outer surface of holder number 14.

The other elements and features of the second embodiment are essentially the same as those described in the first embodiment and are denoted using the same numerical designation. Thus, guide tube 10, spiral electrode 20, second electrode 22, first and second electrode wires 16 and 18, and flexible drive tube 54 with slots 52 which receive electrode 22 to rotate holder 14' and screw spiral electrode 20 into a fetal epidermis are all provided in the second embodiment and shown in FIG. 7. Holder member 14' like holder member 14 is made of insulating material which electrically isolates the electrodes from one another. Holder member 14' is attached to the tubular portion 74 and relative axial movement between them is prohibited as contrasted to the permitted axial movement between the protective cap 56 and holder member 14 of the first embodiment. The diameter of holder member 14' together with the thickness of tubular portion 74 which surrounds holder member 14' approximates the inner diameter of guide tube 10 as shown in FIG. 5.

FIGS. 7-8 illustrate the second embodiment in actual use. The position of the protective cover within guide tube 70 as the physician inserts the fetal electrode product is shown in FIG. 7. The flexible, flared portion 72 is forced to collapse inward and is compressed by guide tube 10. The physician inserts the guide tube through the woman's vagina and cervix until guide tube 10 makes contact with the fetal head or other portion of the fetus. Once contact is made, the doctor holds guide tube 10 stationary and pushes drive tube 54 so that protective cover 70 has passed from within the guide tube. The flared portion 72 which is no longer compressed inward by guide tube 10 returns to its pre-compressed shape shown in FIG. 5 and continues to surround spiral electrode 20 protecting the mother and fetus. When the doctor feels that spiral electrode 20 has contacted the portion of the fetal epidermis to which attachment is to be made, he rotates the drive tube 54 as in the first embodiment and drives spiral electrode 20 into the fetal epidermis.

After the flared portion 72 makes initial contact with the fetal epidermis, the physician continues to rotate the drive tube 54 to drive electrode 20 in place. The flared portion 72 is gradually flattened outwardly upon the fetal epidermis as electrode 20 is rotated into the fetal epidermis, as can be seen in FIG. 8. From the position where flared portion 72 first makes contact with the fetal epidermis through the position of complete attachment of the fetal electrode product, flared portion 72 surrounds electrode 20.

Once the spiral electrode 20 is attached, the guide tube 10 and drive tube 54 can be removed leaving electrode 20 surrounded by flared portion 72 and connected to the fetal epidermis.

When it is desired to remove electrode 20 from the fetus either before, during or after birth, with one hand the physician grasps and twists wires 16, 18 and holder 14' in a counterclockwise direction. Once spiral electrode 20 is unscrewed, flared portion 72 is no longer pushed outwardly and returns to its initial shape, sheathing the electrode coil. Electrode coil 20 is therefore not likely to contact either the physician or the mother, and the electrode can be removed without fear of injury as in the first embodiment.

What is claimed is:

1. A fetal electrode product, comprising a guide tube, an electrode assembly having a holder member with a forward end and a spiral electrode extending from said forward end, a flexible drive tube extending through said guide tube and adapted to engage said electrode assembly for rotating said spiral electrode, a protective cap enveloping said spiral electrode and extending forwardly from the electrode assembly beyond the pointed edge of the electrode so as to protect a user from inadvertent contact with the pointed electrode, said protective cap being displaceable so that the point of the electrode is automatically exposed when the electrode is rotated for attachment to the fetus, and retaining means for irremovably retaining said cap on said holder member during normal use of the electrode product, said cap having an inner surface and said holder member having an outer surface, said retaining means including threads on the inner surface of the cap which engage corresponding threads on the outer surface of said holder member whereby rotation of the holder member will cause displacement of the electrode assembly relative to said cap.

2. A fetal electrode product according to claim 1, wherein said holder member further includes a rearward end located opposite said forward end and wherein said retaining means further includes stop means on the outer surface of said holder member for limiting the movement of said cap relative to said holder member in the direction toward the rearward end of said holder member.

3. A fetal electrode product according to claim 1, wherein said holder member further includes an enlarged head at said forward end, said head containing said corresponding threads on the outer surface and functioning to limit the movement of said cap in the direction toward the forward end of said holder member.

4. A fetal electrode product according to claim 2, wherein said holder member further includes an enlarged head at said forward end, said head containing said corresponding threads on the outer surface and functioning to limit the movement of said cap in the direction toward the forward end of said holder member.

* * * * *